United States Patent [19]
Haining

[11] Patent Number: 5,709,669
[45] Date of Patent: Jan. 20, 1998

[54] BLOOD DRAWING DEVICE

[76] Inventor: Michael L. Haining, 6731 Ashmore, Houston, Tex. 77069

[21] Appl. No.: 573,723

[22] Filed: Dec. 18, 1995

Related U.S. Application Data

[63] Continuation of Ser. No. 219,440, Mar. 29, 1994, abandoned.

[51] Int. Cl.⁶ ..................................................... A61M 5/00
[52] U.S. Cl. ............................................ 604/232; 604/198
[58] Field of Search .................................. 604/192, 195, 604/198, 110, 232, 240, 241, 201, 187, 411; 128/767, 765

[56] References Cited

U.S. PATENT DOCUMENTS

| | | | |
|---|---|---|---|
| 4,758,231 | 7/1988 | Haber et al. | 604/198 |
| 4,892,107 | 1/1990 | Haber | 128/763 |
| 5,024,660 | 6/1991 | McNaughton | 604/110 |
| 5,038,794 | 8/1991 | Van Valkenburg | 128/763 |
| 5,120,311 | 6/1992 | Sagstetter et al. | 604/110 |
| 5,137,521 | 8/1992 | Wilkins | 604/198 |
| 5,222,947 | 6/1993 | D'Amico | 604/198 |
| 5,445,620 | 8/1995 | Haber et al. | 604/232 |

*Primary Examiner*—Michael Powell Buiz
*Assistant Examiner*—A. T. Nguyen
*Attorney, Agent, or Firm*—Richard L. Moseley

[57] ABSTRACT

A blood collection device for use with vacuum sample tube is provided having a retractable carrier for a double cannula. A sliding tab is mounted to the carrier by an outwardly biased flexible member and extends through a longitudinal slot in the barrel. Near either end of the slot V notches are provided in the internal wall of the barrel to engage locking hubs on the sliding tab to releasably lock the carrier in either the exposed or retracted position. A first cap is provided to cover the original open end and a second cap is provided to cover the end left open after retraction of the double cannula into the barrel.

8 Claims, 3 Drawing Sheets

BLOOD DRAWING DEVICE

This application is a continuation of application Ser. No. 08/219,440, filed Mar. 29, 1994, now abandoned.

BACKGROUND OF THE INVENTION

1. Field of the Invention

The present invention relates to devices used to withdraw blood into vacuum tubes for testing. More particularly the invention relates to a device to which a double ended cannula is attached and for receiving the vacuum tube which is pierced by one of the cannula, the other end being inserted into the subject's vein. Most particularly the invention relates to a blood drawing device in which the cannula may be withdrawn into the device and the device closed after use.

2. Related Information

The advent of the AIDS virus has focused attention on diseases which are transmitted by contact with contaminated blood. Many devices are now available on the market to reduce the likelihood of such contact. More particularly there have been devices for retracting the needles of hypodermic syringes into the barrel after use as exemplified in my own U.S. Pat. Nos. 4,790,822; 4,950,251 and 5,152,750. Additionally the insertion cannula of a catheter has also been made retractable as in my U.S. Pat. No. 5,019,049.

Until recently no one has addressed the problem associated with withdrawing blood samples from patients for subsequent testing. The blood drawing device generally consists of a cylindrical barrel open at one end and having a double cannula mounted on the end opposite the open end. The double cannula includes two sharp needles mounted together with a passage way connecting the two. One end of the cannula is inserted into the patient's arm the other, extending into the cylindrical barrel of the blood drawing device, pierces the puncture pad on the end of a blood sample tube. The blood sample tube is generally shipped with a slight vacuum which is sealed inside by the puncture pad. The vacuum assists in drawing the blood into the tube. A typical double cannula is a VACUTAINER BRAND MULTIPLE SAMPLE NEEDLE as manufactured by Becton-Dickson, Inc.

A disposable blood collection device is disclosed in U.S. Pat. No. 5,070,885 in which the double cannula is retractable into the device after use. The retracting mechanism as shown is quite cumbersome requiring a rotation to unlock the cannula carrier which is retracted. Additionally, while a cap is provided to close the open rear end of the device, nothing is provided to cover the opposite end which is left open after the carrier and double cannula have been retracted.

It is a feature of the present invention that an easily retractable double cannula carrier is provided within a blood collection device while still providing secure retention of the cannula in the use position.

It is a further feature of the present invention that both open ends of the blood collection device are closed after retraction of the cannula.

SUMMARY OF THE INVENTION

To protect against accidental needle prick a blood collection device is provided wherein the double cannula is retractable within the device after all blood samples are taken. The device comprises a hollow barrel or tube of semi-rigid plastic material into which the double cannula can be retracted after use. A slidable carrier is provided onto which the double cannula may be mounted. A sliding tab is mounted to the carrier by an outwardly biased flexible member and extends through a longitudinal slot in the barrel. Near either end of the slot, V notches are provided in the internal wall of the barrel to engage locking hubs on the sliding tab to releasably lock the carrier in either the exposed or retracted position. A first cap is provided to cover the original open end and a second cap is provided to cover the end left open after retraction of the double cannula into the barrel. Additionally the second cap extends the length of the longitudinal slot to effectively seal the whole device.

DESCRIPTION OF THE PREFERRED EMBODIMENT

For a detailed description of the preferred embodiment the reader is referred to the appended figures in which like components are given like numerals for ease of reference.

Figure 1:
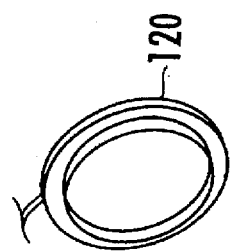
FIG. 1 is and exploded isometric view of one embodiment of the blood collection device of the present invention.
Figure 1:
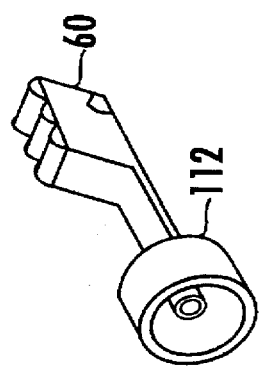
Figure 1:
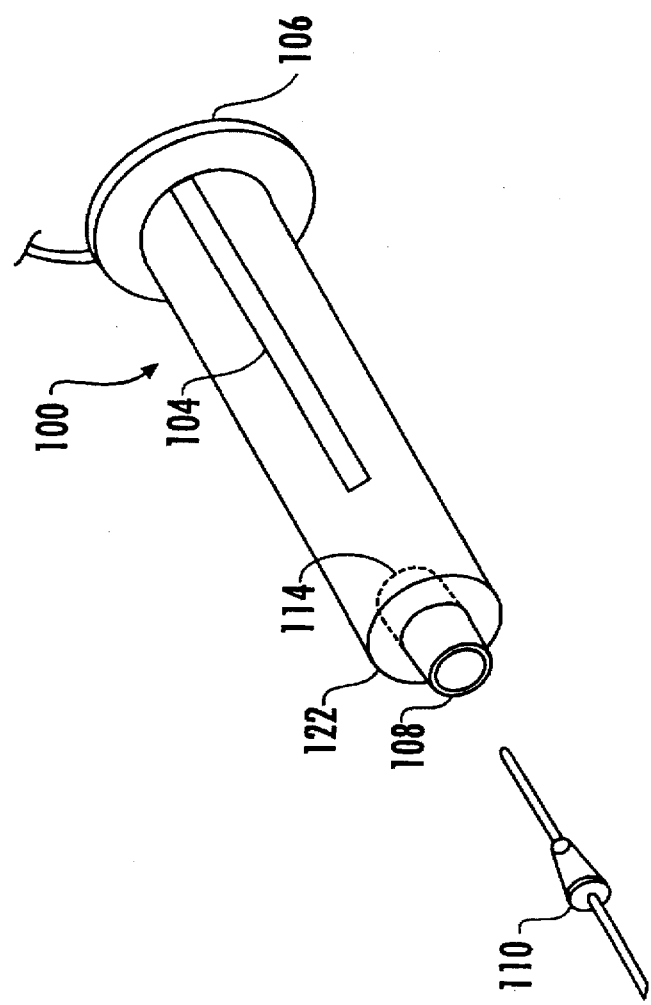

Referring first to FIG. 1 there is shown an exploded isometric view of one embodiment of the invention. The invention is shown to comprise a hollow cylindrical barrel 102 having a logintudinal slot 104 extending part way between the two ends. A finger flange 106 is provided for ease of handling at the distal end. The distal end is open while the opposite or insertion end is shown to be partially closed by annular surface 122. Extending axially outward from annular surface is cylindrical projection 108 and extending inward is cylindrical projection 114. A carrier 112 is provided for slidable mounting within the barrel 102. A double cannula 110 is provided for mounting on the carrier 112. The carrier includes a tab 60 which extends through slot 104. Finally a cap 120 is provided to plug the open distal end of the barrel after use.

Figure 2:
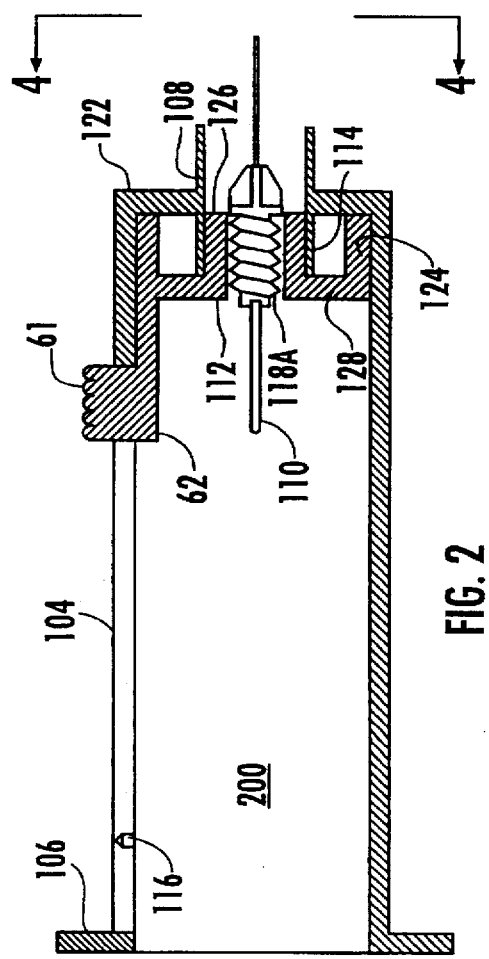
FIG. 2 is a side elevational view in cross section showing the double cannula in the exposed position.

Referring now to FIG. 2 a partial cross sectional view of one embodiment of the invention is shown. The hollow barrel 102 defines a chamber 200 for receiving a vacuum blood sample drawing tube (not shown). The distal end of the barrel is completely open while the insertion is partially closed by annular surface 122. Extending outward from annular surface is projection 108 and extending inward is projection 114. Longitudinal slot 104 extends from near distal end to flanged end. Near either end and on both sides of slot 104 are notches 116 and 116A (See FIG. 7 for location of notch 116A which is hidden by tab 60 in FIG. 2). Longitudinal slot is more clearly shown in FIG. 3 which is the embodiment shown in FIG. 2 rotated 90°. The location of notches 116 and 116A are shown in dashed lines.

Carrier 112 is shown to have a back 128 from which extends to hollow cylinders 124 and 126. The internal surface of inner cylinder 126 is provided with threads 118A. The outer surface of internal cylinder 126 fit snugly against the inner surface of projection 114. The outer surface of outer cylinder 124 fits snugly against the inner surface of the barrel. The double cannula 110 is threadedly connected to carrier.

Figure 5:
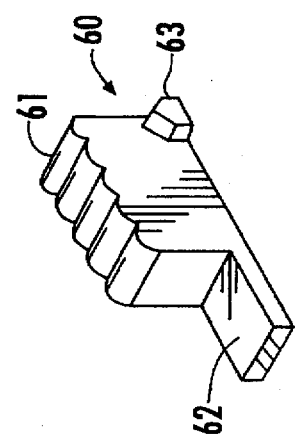
FIG. 5 is a perspective view of the sliding tab showing one of the locking hubs for locking the carrier in the exposed or retracted position.

The carrier 112 is slidably mounted within the barrel 102 having the sliding tab 60 mounted thereto by base flexible member 62 biasing the tab outward to extend through slot 104. Referring now to FIG. 5 the tab 60 is shown to have V topped hubs 63 and 64 on either side (only one shown in FIG. 5). As member 62 biases tab outward V topped hubs 63 and 64 are forced into releasable locking engagement with either of V shaped notches 116 or 116A.

Figure 4:
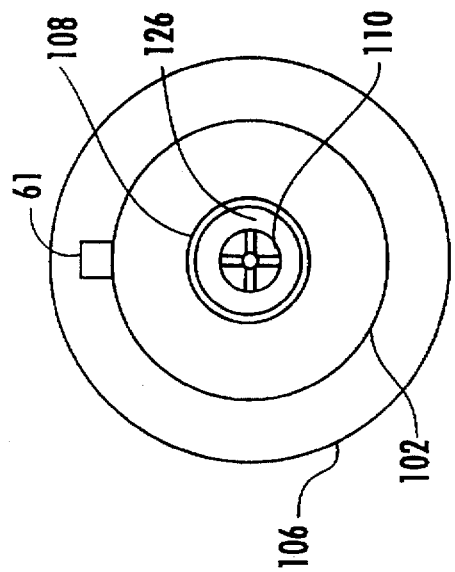
FIG. 4 is view taken along line 4—4 in FIG. 1.
Figure 3:
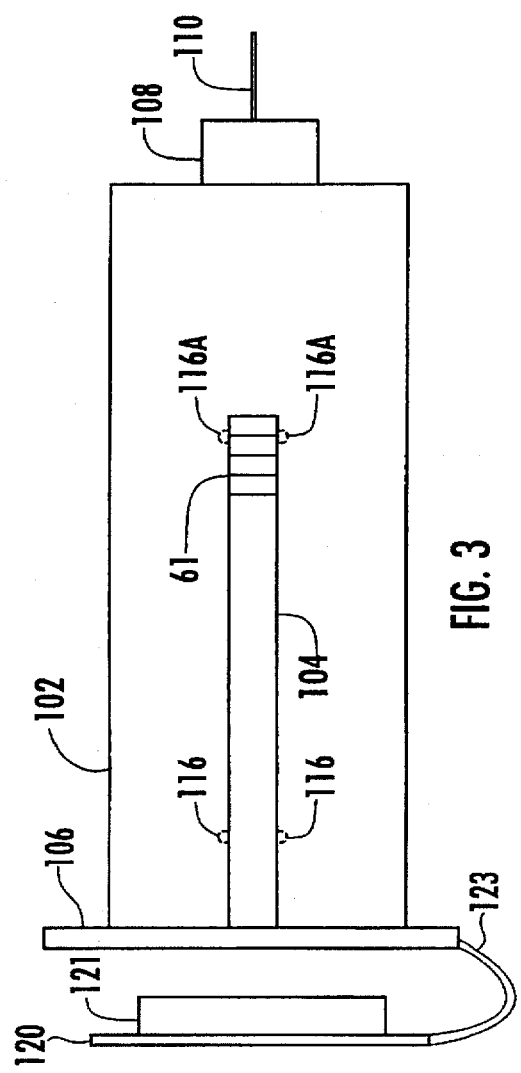
FIG. 3 is a top view of the blood collection device with the double cannula in the exposed position.

FIG. 4 a view taken along line 4—4 of FIG. 2 and is included for clarity. FIG. 3 is an overall view of the embodiment shown in FIG. 2 rotated 90° and showing the cap 120 connected to the flange 106 by flexible strap 123. The cap 120 also includes annular projection 121 the outer surface of which snugly fits against the inner surface of barrel 102 when inserted.

Figure 6:
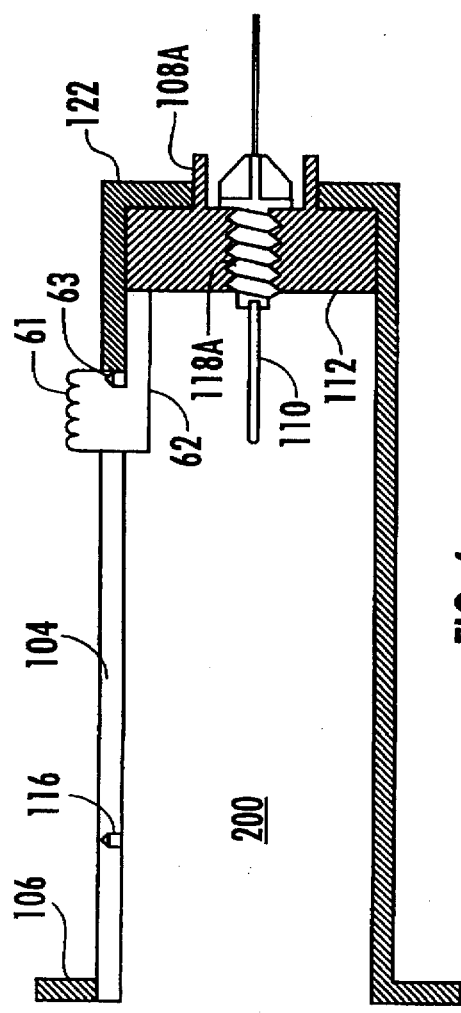
FIG. 6 is a side elevational view in cross section showing showing a second embodiment with the double cannula in the exposed position.
Figure 7:
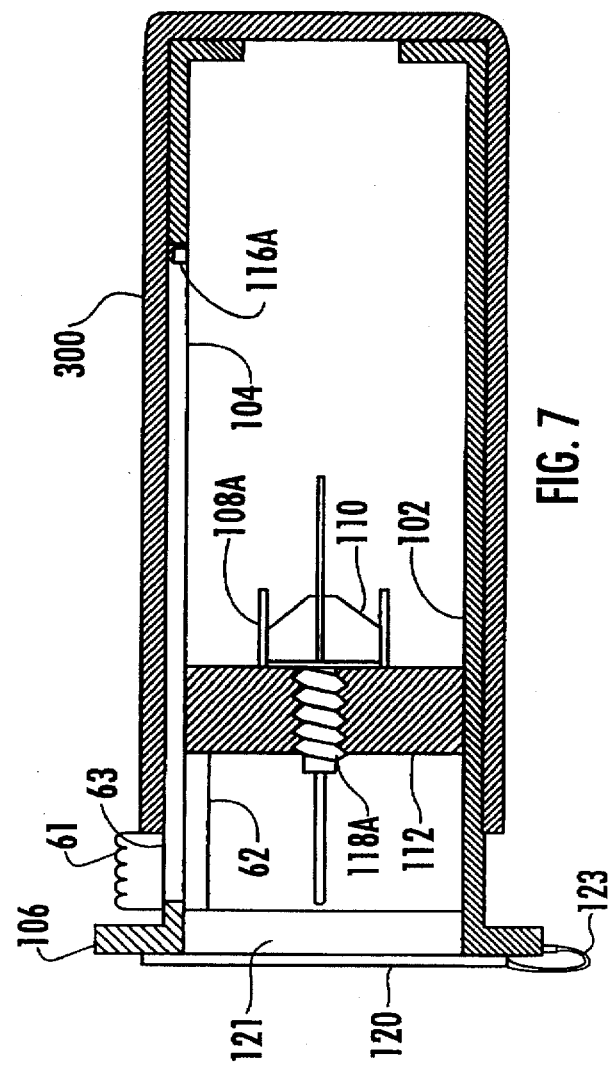
FIG. 7 is a side elevational view in cross section showing the embodiment of FIG. 6 with the double cannula in the retracted position and with both caps in place.

Referring now to FIGS. 6 and 7 a second embodiment of the blood drawing device is shown. The carrier 112 of this embodiment is provided with the cylindrical projection 108A which extends through opening in annular surface 122. The projection 108 provides additional stability for carrier during use.

More particularly FIG. 7 illustrates the blood drawing device with the carrier 112 retracted within the barrel 102. Cap 120 is shown with annular projection 121 inserted within barrel 102 to effectively close the open flanged end. Additionally a second cap 300 is shown to cover the opposite end and up to the tab 60 over the slot 104. The double cannula 110 is retracted and the whole system is essentially a closed sharps container.

Figure 8:
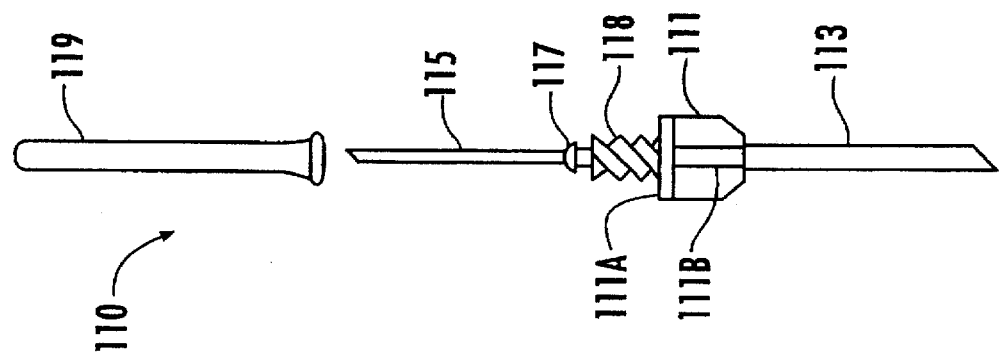
FIG. 8 is a side elevational view of a typical double cannula as used with the present invention.

FIG. 8 is an elevational view of a typical double cannula as manufactured by Becton-Dickson and sold under the VACUTAINER brand. There is shown a base 111 having a flange 111A on one side and a ribbed projection 111B on the opposite side. A first cannula 113 extends from ribbed projection 111B and an externally threaded projection 118 extends from the flange 111A. A tip 117 extends from the threaded projection 110 and a second cannula 115 extends from tip 117. The two cannulae are connected by a passage way in base (not shown). Finally a rubber cover 119 is provided which engages tip 117 when placed over second cannula 115.

In use the caps 120 and 300 are removed and the carrier is secured at end 122. The proper double cannula is selected and mounted to the carrier and the first cannula 113 inserted into the patient. The vacuum blood container (not shown) is then inserted until the second cannula 115 pierces the puncture pad on the tube and the tube is filled. As many sample tubes as required are filled. When the last tube is filled the first cannula 113 is removed from the patient and the carrier retracted into the rear position. The two caps 120 and 300 may then be placed over the ends.

The invention claimed is:

1. A blood collection device comprising
   a hollow cylindrical barrel having an insertion end and a distal end, said barrel including
   (1) a longitudinal slot partially extending between said ends, and
   (2) internal locking notches in the internal surface of said barrel and near either end of said barrel;
   a carrier slidably mounted within said barrel adapted to receive a double cannula, said carrier having an axial length substantially shorter than said barrel; and
   a rigid sliding member extending through said slot and fixedly attached to said carrier by an outwardly biased flexible member, said flexible member having a locking ridge on at least one side that is releasably locked into either of said locking notches by said biased member.

2. The blood collection device of claim 1 further comprising a cap connected to said distal end by a flexible strap to close said distal end.

3. The blood collection device of claim 1 further comprising a cap that is removably securable over said insertion end after said rigid sliding member is retracted and locked into said notch near said distal end to close said insertion end and substantially cover said slot.

4. The blood collection device of claim 1 further comprising a double cannula threadedly connected to said carrier such that a first cannula extends through said insertion and a second cannula extends within said barrel.

5. A blood collection device comprising
   a hollow cylindrical barrel having an insertion end and a distal end, said barrel including
   (1) a longitudinal slot partially extending between said ends, and
   (2) internal locking notches in the internal surface of said barrel and near either end of said barrel;
   a carrier slidably mounted within said barrel adapted to receive a double cannula, said carrier having an axial length substantially shorter than said barrel;
   a rigid sliding member extending through said slot and fixedly attached to said carrier by an outwardly biased flexible member, said flexible member having a locking ridge on at least one side that is releasably locked into either of said locking notches by said biased member; and
   a double cannula threadedly connected to said carrier such that a first cannula extends through said insertion end and a second cannula extends within said barrel.

6. The blood collection device of claim 5 further comprising a cap that is removably securable over said insertion end after said rigid sliding member is retracted and locked into said notch near said distal end to close said insertion end and substantially cover said slot.

7. A blood collection device comprising
   a hollow cylindrical barrel having an insertion end and a distal end, said barrel including
   (1) a longitudinal slot partially extending between said ends, and
   (2) internal locking notches in the internal surface of said barrel and near either end of said barrel;
   a carrier slidably mounted within said barrel adapted to receive a double cannula, said carrier having an axial length substantially shorter than said barrel;
   a rigid sliding member extending through said slot and fixedly attached to said carrier by an outwardly biased flexible member, said flexible member having a locking ridge on at least one side that is releasably locked into either of said locking notches by said biased member;
   a first cap connected to said distal end by a flexible strap to close said distal end; and
   a second cap that is removably securable over said insertion end after said rigid sliding member is retracted and locked into said notch near said distal end to close said insertion end and substantially cover said slot.

8. A blood collection device comprising a hollow cylindrical barrel having an insertion end and a distal end, said barrel including
- (1) a longitudinal slot partially extending between said ends, and
- (2) internal locking notches in the internal surface of said barrel and near either end of said barrel;

a carrier slidably mounted within said barrel adapted to receive a double cannula, said carrier having an axial length substantially shorter than said barrel;

a rigid sliding member extending through said slot and fixedly attached to said carrier by an outwardly biased flexible member, said flexible member having a locking ridge on at least one side that is releasably locked into either of said locking notches by said biased member;

a double cannula threadedly connected to said carrier such that a first cannula extends through said insertion end and a second cannula extends within said barrel;

a first cap connected to said distal end by a flexible strap to close said distal end; and a second cap that is removably securable over said insertion end after rigid sliding member is retracted and locked into said notch near said distal end to close said insertion end and substantially cover said slot.

* * * * *